United States Patent
Raees et al.

(10) Patent No.: US 6,596,487 B2
(45) Date of Patent: Jul. 22, 2003

(54) MUTATION DETECTION USING DENATURING GRADIENTS

(75) Inventors: Saeedullah Mohammad Raees, Cupertino, CA (US); Brian Alfred Perry, Fremont, CA (US)

(73) Assignee: Ana-Gen Technologies, Inc., Atlanta, GA (US)

(*) Notice: Subject to any disclaimer, the term of this patent is extended or adjusted under 35 U.S.C. 154(b) by 0 days.

(21) Appl. No.: 09/804,589

(22) Filed: Mar. 12, 2001

(65) Prior Publication Data

US 2002/0042060 A1 Apr. 11, 2002

(Under 37 CFR 1.47)

Related U.S. Application Data

(60) Provisional application No. 60/188,534, filed on Mar. 10, 2000.

(51) Int. Cl.[7] .............. C12Q 1/68; C12P 19/34; B01D 57/02; C07H 21/02; C07H 21/04

(52) U.S. Cl. .............. 435/6; 435/91.1; 204/450; 204/456; 536/23.1; 536/24.3; 536/24.33

(58) Field of Search .............. 435/6, 91.1, 183; 436/94, 501; 536/23.1, 24.3, 24.32, 25.3, 25.32, 25.4; 204/450, 456, 466, 469

(56) References Cited

U.S. PATENT DOCUMENTS

| | | | |
|---|---|---|---|
| 5,413,908 A | 5/1995 | Jeffreys ........................ | 435/6 |
| 5,683,872 A | * 11/1997 | Rudert et al. | |
| 5,942,390 A | * 8/1999 | Cominelli et al. | |
| 6,107,026 A | 8/2000 | Lange, III et al. .............. | 435/6 |
| 6,110,709 A | 8/2000 | Ausubel et al. ............ | 435/91.2 |
| 6,153,013 A | 11/2000 | Sakai et al. .................. | 118/719 |
| 6,180,536 B1 | 1/2001 | Chong et al. ............... | 438/745 |
| 6,186,660 B1 | 2/2001 | Kopf-Sill et al. .............. | 435/6 |

FOREIGN PATENT DOCUMENTS

| | | |
|---|---|---|
| WO | WO 00/18960 | 4/2000 |
| WO | WO 00/50869 | 8/2000 |
| WO | WO 00/56925 | 9/2000 |
| WO | WO 00/61801 | 10/2000 |
| WO | WO 00/61805 | 10/2000 |
| WO | WO 01/11351 | 2/2001 |

OTHER PUBLICATIONS

M.L. Fontaneo, et al., Process of analyzing nucleic acids by Hybridization and a device for its implementation, FLS, inc. pp. 1–41.*

* cited by examiner

Primary Examiner—Ethan Whisenant
Assistant Examiner—Frank Lu
(74) Attorney, Agent, or Firm—McGinn & Gibb, PLLC; Mohammed S. Rahman, Esq.

(57) ABSTRACT

Methods for detecting single nucleotide polymorphisms in a sample by applying an energy gradient to a mixture of probe-hybridized target wild type and mutant polynucleotides are provided. A nucleotide probe, having a nucleotide sequence complementary to at least a portion of the wild type or mutant polynucleotide(s), is exposed to a sample containing target wild type polynucleotide(s) and target mutant polynucleotide(s) under hybridizing conditions. Target wild type polynucleotide(s) form homoduplexes with the wild type probe, while target mutated polynucleotide(s) form heteroduplexes with the wild type probe. Target mutant polynucleotide(s) form homoduplexes with the mutant probes, while target wild type polynucleotide(s) form heteroduplexes with the mutant probe. An energy gradient is applied to the duplex-containing sample to induce selective denaturation of the duplexes. The gradient may be a thermal or chemical one and is preferably temporally linear. The hetero- and homoduplexes deanneal at different times so that the detection of more than one type of polynucleotide(s) is indicative of a single nucleotide polymorphism. Capillary electrophoresis, gel electrophoresis, high performance liquid chromatography, or microfluidics are typically used for identification of the separated strands.

15 Claims, 4 Drawing Sheets

MUTATION DETECTION USING DENATURING GRADIENTS

RELATED APPLICATIONS

This application claims priority from U.S. Provisional Patent Application 60/188,534 filed Mar. 10, 2000, incorporated by reference herein.

FIELD

The present invention relates generally to the field of genetic analysis, particularly to the detection of single nucleotide polymorphisms.

BACKGROUND

The human genome is made up of approximately 30,000 unique genes, which control the development and characteristics of the mature human. Each gene is composed of a sequence of nucleotides which are generally conserved across the species and are referred to as wild type. Single nucleotide polymorphisms (SNPs) are nucleotide sequence variants from the predominant wild type. Typically, single nucleotide polymorphisms are associated with expressed mutations. There is considerable interest in the development of methods which permit the rapid, accurate identification of single nucleotide polymorphisms.

Singh and Ullman in WO/056925 (Aclara Biosciences, Sep. 28, 2000) describe methods for single nucleotide polymorphism detection using complementary coded primers and differentially labeled terminating nucleotides.

Arnold, Theriault and Bedilion in WO/050869 (Incyte Pharmaceuticals, Aug. 31, 2000) describe methods for detecting multiple single nucleotide polymorphisms in a sandwich assay employing SNP probes.

Nerenberg, Canter and Radtkey in WO/061805 (Nanogen/Becton Dickinson Partnership, Oct. 19, 2000) describe methods for the analysis of SNPs using an electronically bioactive microchip.

Takenaka in WO/111351 (Feb. 15, 2001) describes a method for detecting SNPs using gold electrodes formed on the bottom face of a chip.

Despite these advances, there remains a need for an accurate, simple method for the detection of single nucleotide polymorphisms.

SUMMARY

The present invention provides methods for detecting single nucleotide polymorphisms in a sample by applying an energy gradient to a mixture of probe-hybridized target wild type and mutant polynucleotides.

A nucleotide probe, having a nucleotide sequence complementary to at least a portion of one strand of either the target wild type or target mutant polynucleotide(s), is exposed to a sample containing target wild type polynucleotide(s) and target mutant polynucleotide(s) under hybridizing conditions. If a wild type probe is used, target wild type polynucleotide(s) will form homoduplexes with the wild type probe, while target mutant polynucleotide(s) will form heteroduplexes with the wild type probe. If a mutant probe is used, target mutant polynucleotide(s) will form homoduplexes with the mutant probe, while target wild type polynucleotide(s) will form heteroduplexes with the mutant probe. Either the probe or the target may be attached to a suitable solid support.

An energy gradient is applied to the duplex-containing sample to induce selective denaturation of the duplexes. The gradient may be a thermal or chemical one and is preferably temporally linear. The hetero- and homo-duplexes deanneal at different times so that the detection of more than one type of polynucleotide(s) is indicative of a single nucleotide polymorphism. Preferably, a reference homozygous wild type is used as a control. In those cases in which both alleles of a test sample are mutant, only a single eluent peak or signal will be detected. The presence of mutation may be confirmed by comparing the elution time to that of the control.

Capillary electropheresis, gel electropheresis, high performance liquid chromatography, or microfluidics are typically used for identification of the separated strands.

DETAILED DESCRIPTION OF THE INVENTION

Figure 1:
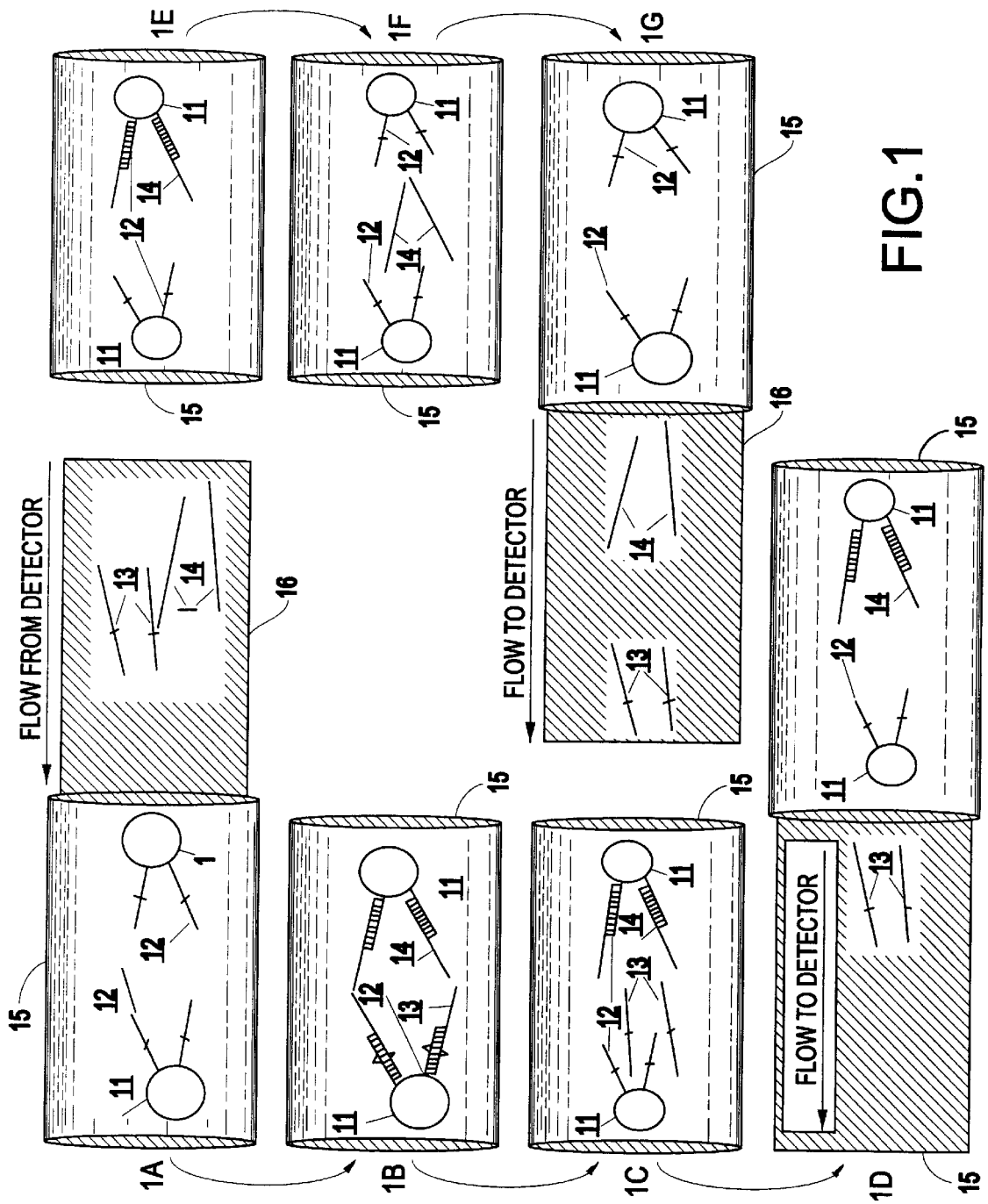
FIG. 1A, depicts silica bead (11) and immobilized probe (12) in an HPLC column or other suitable reaction cartridge (15) with target mutant nucleic acid (13) and target wild type nucleic acid (14), being loaded onto cartridge (15) with the flow of eluent (16).
FIG. 1B depicts immobilized probe (12), target mutant nucleic acid (13) and target wild type nucleic acid (14) subjected to hybridization conditions, representing the hybridization product of target mutant nucleic acid (13) and probe (12) as a heteroduplex and the hybridization product of target wild type nucleic acid (14) and probe (12) as a homoduplex, both suspended in eluent (16) contained within an HPLC column or other suitable reaction cartridge (15).
FIG. 1C illustrates the denaturation of the heteroduplex hybridization product, whereby probe (12) is separated from target mutant nucleic acid (13) under deannealing conditions. Deannealing conditions are imposed by suitable means such as controlling temperature, the concentration of chemical denaturants (e.g., urea, formamide, NaOH etc), ionic strength, and/or the pH of eluent (16) in HPLC column (15).
FIG. 1D shows deannealed target mutant nucleic acid (13) migrating into the flow path of eluent (16). The Figure also represents intact homoduplex (14) contained within HPLC column (15) along with free bead (11) and immobilized probe (12).
FIG. 1E depicts the intact homoduplex hybridization product of target wild type nucleic acid (14), probe (12) and bead (11) contained within cartridge (15).
FIG. 1F illustrates the homoduplex hybridization product, silica bead (11), immobilized probe (12) and target wild type nucleic acid (14) undergoing deannealing conditions. Deannealing conditions are imposed by suitable means such as controlling temperature, the concentration of chemical denaturants (e.g., urea, formamide, NaOH etc), ionic strength, and/or the pH of eluent (16) in HPLC column (15).
FIG. 1G represents deannealed homoduplex. The target wild type nucleic acid (14) has deannealed from immobilized probe (12) and left HPLC column (15), migrating into the flow path of eluent (16). Free silica beads (11) and immobilized probes (12) remain in the HPLC column (15).
Figure 2:
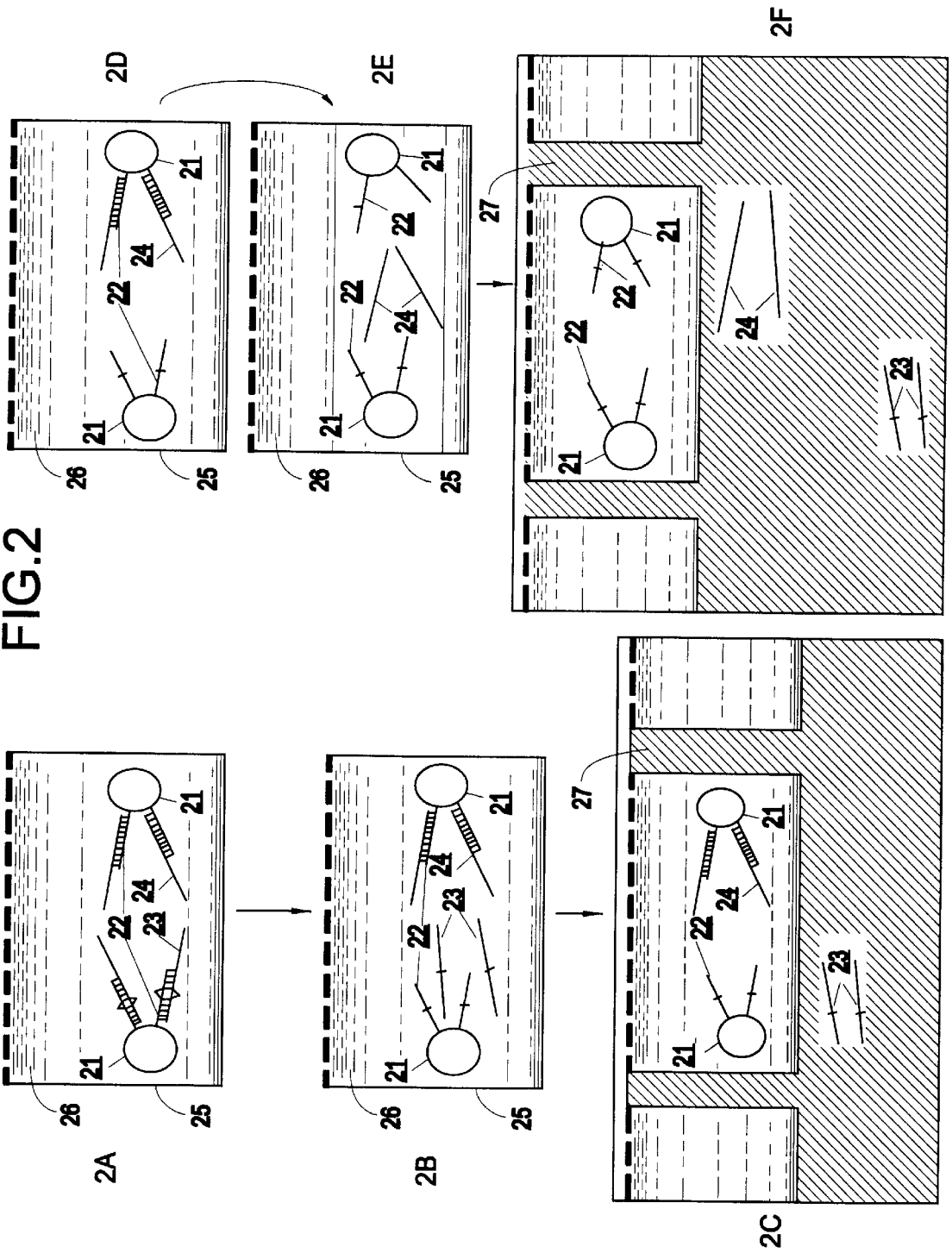
FIG. 2A depicts hybridization products comprising target mutant nucleic acids (23) and target wild type nucleic acids (24) bound to probes (22) on beads (21). Beads (21) will have at least one probe (22) and preferably a plurality of probes (22). The hybridization product of target mutant nucleic acid (23) and probe (22) is heteroduplex and the hybridization product of target wild type nucleic acid (24) and probe (22) is homoduplex. These products are suspended in buffer (26) contained within a well (25) of an electrophoresis gel.
FIG. 2B illustrates the heteroduplex hybridization product of silica beads (21) and target mutant nucleic acid (23) undergoing deannealing conditions. Deannealing conditions are imposed by suitable means such as controlling temperature, the concentration of chemical denaturants (e.g., urea, formamide, NaOH etc), ionic strength, and/or the pH of running buffer (26) contained in well (25).
FIG. 2C represents target mutant nucleic acid (23) deannealed from immobilized probe (22) leaving the well (25) and migrating into the gel (27) matrix due to the applied voltage across the gel (27). The Figure also shows intact homoduplex contained within the well (25) along with free silica bead (21) and immobilized probe (22).
FIG. 2D depicts the intact homoduplex hybridization product of target wild type nucleic acid (24) with probe (22) on silica bead (21), free silica bead (21) and immobilized probe (22).
FIG. 2E illustrates the homoduplex hybridization product, with target wild type nucleic acid (24) undergoing deannealing conditions. Deannealing conditions are imposed by suitable means such as controlling temperature, the concentration of chemical denaturants (e.g., urea, formamide, NaOH etc), ionic strength, and/or the pH of running buffer (26) contained in well (25).
FIG. 2F represents target wild type nucleic acid (24) deannealed from immobilized probe (22) leaving the well (25) and migrating into the gel (27) matrix, due to the applied voltage across the gel (27). The Figure also represents free silica bead (21) with immobilized probe (22) remaining in the well (25).
Figure 3:
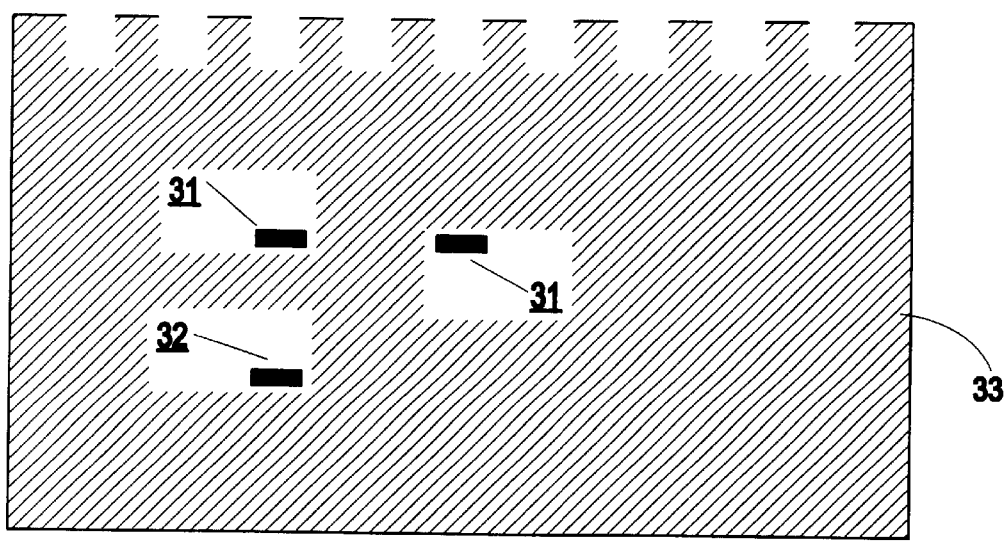
FIG. 3 depicts target mutant nucleic acid (32) separating in an electrophoresis gel (33) from target wild type nucleic acid (31).
Figure 4:
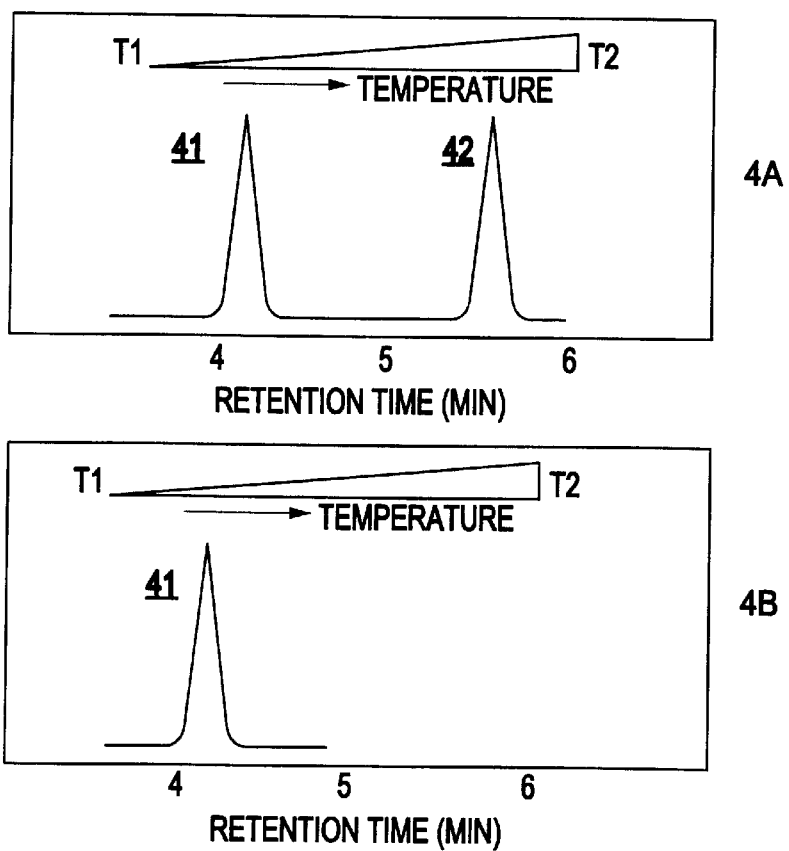
FIG. 4A represents an HPLC profile of the target mutant nucleic acid (42) and target wild type nucleic acid (41), showing 2 distinct peaks. Temperature gradient T11 T2 is shown at the top of the Figure.
FIG. 4B illustrates an HPLC profile of target wild type nucleic acid (41) showing only one peak, along with the temperature gradient.
Figure 5:
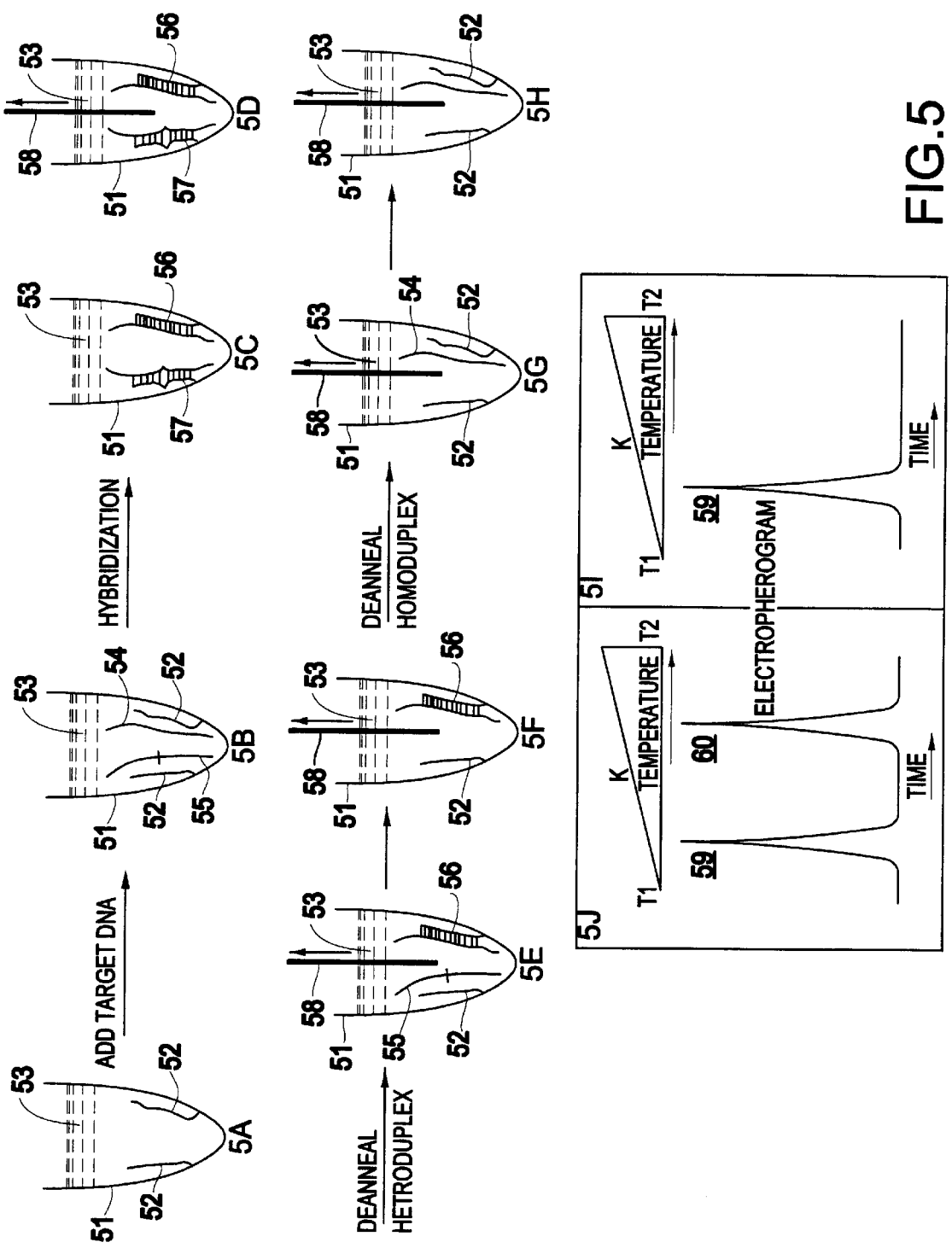
FIG. 5A depicts microwell (51) having immobilized probes (52) and media (53).
FIG. 5B depicts denatured target wild type nucleic acid (54) and target mutant nucleic acid (55) added to the microwell (51) for hybridization with probes (52) in media (53).
FIG. 5C shows microwell (51), representing the heteroduplex hybridization product (57) of target mutant nucleic acid (55) and probe (52) and the homoduplex hybridization product (56) of target wild type nucleic acid (54) and probe (52), suspended in buffer (53).
FIG. 5D depicts the microwell of FIG. 5C with an electrophoresis capillary inserted into well (51). The arrow indicates the direction of electrophoretic mobility.
FIGS. 5E & 5F illustrate the heteroduplex hybridization product (57) undergoing deannealing conditions. Deannealing conditions are imposed by suitable means such as controlling temperature, the concentration of chemical denaturants (e.g., urea, formamide, NaOH etc), ionic strength, and/or the pH of buffer (16) in microwell (51). The target mutant nucleic acid (55) has deannealed from immobilized probe (52) and left microwell (51) and migrated into the electrophoresis capillary (58). The arrow indicates the direction of electrophoretic mobility of target mutant nucleic acid (55). The homoduplex (56) is still intact and contained within microwell (51).
FIGS. 5G & 5H illustrate the homoduplex hybridization product (56) undergoing deannealing conditions. Deannealing conditions are imposed by suitable means such as controlling temperature, the concentration of chemical denaturants (e.g., urea, formamide, NaOH etc), ionic strength, and/or the pH of buffer (53) microwell (51). The target wild type nucleic acid (54) has deannealed from immobilized probe (52) and left microwell (51) and migrated into the electropheresis capillary (58) due to the applied voltage across the capillary (58). The arrow indicates the direction of electrophoretic mobility of target wild type nucleic acid (54). Immobilized probe (52) remains in microwell (51).
FIGS. 5I & J, represent electropherograms of the target mutant nucleic acid (55) and target wild type nucleic acid (54). When a single strand mutation is present, electropheresis will show two distinct peaks (59 for wild type & 60 for mutant). The chart K represents the temperature gradient imposed upon the microwell (51).

The invention will now be described in detail by way of reference only using the following definitions and description. All patents and publications referred to herein are expressly incorporated by reference.

Definitions

As used herein, the following terms and abbreviations, whether used in the singular or plural, have the meanings indicated.

The term "heteroduplex" refers to the hybridization product of a wild type oligonucleotide probe with the sense or antisense strand of a target gene or polynucleotide having at least one nucleotide variant from the predominant wild type gene or polynucleotide. Alternatively, the heteroduplex may be the hybridization product of a mutant oligonucleotide probe with the sense or antisense strand of a target wild type gene or polynucleotide The term "homoduplex" refers to the hybridization product of a wild type oligonucleotide probe with the sense or antisense strand of a target wild type gene or polynucleotide. The homoduplex may also be the hybridization product of a mutant probe with a mutant target.

The term "linear thermal denaturant gradient" means a constant rate of increase in temperature per unit time over the entire period during which the temperature is increased (first order kinetics). "T1" is defined as the starting temperature of the temperature gradient and may be either ambient (room) temperature or any temperature lower than the lowest Tm (deannealing T) of any heteroduplex present in the sample being analyzed. "T2" is defined as the final temperature of the temperature gradient and is any temperature greater than the highest Tm of any homoduplex present in the sample being analyzed. T2 will generally be 5–10° C. above the highest homoduplex Tm present in the sample being analyzed. The time of the gradient is determined by several factors, such as format employed (e.g., CE, PAGE or HPLC), desired resolution, number of different loci being screened, et al.

The term "linear chemical denaturant gradient" means a constant rate of increase over time in the concentration of chemical reagents, such as urea, formamide, NaOH, etc. which disrupt hydrogen bonding between double-stranded nucleic acid duplexes. The concentration of denaturant is increased in such a manner that the incremental increase in molarity per unit time is constant over the entire period in which the denaturant concentration is increased ($\Delta D = k\Delta t$). "D1" is defined as the starting denaturant concentration and "D2" is defined as the final denaturant concentration. D1 may range from a complete absence of denaturant to any concentration sufficiently low to be ineffective in deannealing of any heteroduplex present in the sample being analyzed. D2 is any denaturant concentration sufficient to cause complete disruption of hydrogen bonding and deannealing of any homoduplex with the highest Tm present in the sample being analyzed.

The term "single nucleotide polymorphism" is used herein to describe any nucleotide sequence variant from the predominant wild type. Typically, single nucleotide polymorphisms are associated with expressed mutations.

The term "wild type" refers to a nucleotide sequence associated with the predominant naturally occurring gene.

This invention relates to novel diagnostic or mutation-screening-methods which allows several loci, derived from multiple DNA samples, to be rapidly and simultaneously screened for mutations in discrete areas of specific genes. This invention describes the implementation of this mutation screening method in four different formats: capillary electrophoresis (CE); polyacrylamide gel electrophoresis (PAGE); high performance liquid chromatography (HPLC), and microfluidics. The samples consist of either labeled or unlabeled, single- or double-stranded DNA fragments or "targets" (of various lengths) which have been hydrogen-bonded (annealed) to "probes" consisting of either oligonucleotides (typically 20–40 nucleotides in length) or melting temperature domain-length (typically 50–300 nt) single-stranded DNA fragments immobilized on microscopic and/or macroscopic particles or other substrates of various diameters and chemical compositions. Alternatively, the targets may be immobilized on a solid support. The presence of mutations will generate heteroduplexes containing sites of base mismatch between the probe and target which will substantially lower the melting temperature (Tm) of the heteroduplex compared to the corresponding homoduplex. As a linear temporal temperature or linear temporal chemical denaturant gradient is introduced, the heteroduplexes will be the first to dissociate (deanneal), followed by homoduplex dissociation at a higher temperature or higher denaturant concentration. If the hetero- and homoduplex pair being subjected to the linear temporal temperature or chemical denaturant increase are placed into either an electrical field (CE and PAGE) or the flow of solvent (HPLC), their different times of deannealing and hence, mobilization from the solid supports will allow them to be distinguished from one another as either two different bands in PAGE or as two different peaks in CE and HPLC respectively. Hence, the presence of a mutation or gene sequence changes can be detected by the number of species resolved by this method. As long as the lower (T1) and upper (T2) temperature points or the lower (D1) and upper (D2) denaturant concentrations representing the parameters of the temporal temperature or denaturant gradients are outside of the Tms of all hetero- and homoduplexes represented, many different species of target fragments, derived from many different genes can be simultaneously screened by this method. This method will have considerable utility in clinical diagnostics, determining disease predisposition, research and development and the characterization and mapping of SNPs (single nucleotide polymorphisms).

This invention provides a method for the detection of mutations based upon the different chemical and thermal stabilities of homo- and heteroduplex DNA or cDNA fragments. The inventive process relies upon the recognition that the homo- and heteroduplex complexes are responsive to different denaturing conditions. The imposition of either a linear thermal denaturant gradient (in e.g., CE, PAGE and HPLC formats) or a linear chemical denaturant gradient (in e.g., HPLC and other formats) upon a probe-target duplex results in differential separation of the homo- and heteroduplexes. The probe or target are optionally attached to a solid support, such as a bead or other solid support, as is known in the art. Preferably, the solid support is a silica or polymeric bead or other material capable of being derivatized. The form of the support may be particulate (macroscopic and/or microscopic), filters, membranes, fibers, sheets, solid surfaces (e.g., inner walls of tubes and microwells) and the like. Immobilization may be achieved by means well known in the art, such as by formation of an amide bond, by avidin/streptavidin or biotin/streptavidin attachment, or by synthesis of the probe or PCR primer directly on the solid support. Preferably, but not necessarily, the probe or target incorporates a detection label. Preferred labels include: radioisotopes, chemiluminescent, luminescent and fluorescent agents (fluor), cofactors and the like.

This invention encompasses methods and apparati for performing nucleic acid hybridization on a solid support. The practice of the present invention employs conventional techniques of chemistry, molecular biology, microbiology, and recombinant DNA technology well known to the skilled artisan. Hybridization reactions are preferably performed at a separate work station by adjusting one or more factors influencing hybridization, including temperature, and/or ionic strength and pH.

In one embodiment, a region of a specific wild type gene (or of several different genes) known to be a site of mutational incidence (i.e., a "hot spot") is identified. Next, a probe is synthesized which is fully complementary to this area of the sense strand of the wild type sequence. If the area of the gene harboring the putative mutation(s) is small, or if mutations are known to occur in specific positions, oligonucleotide probes will suffice. The probe is designed to encompass the putative site of mutation by placing it either in the middle of the oligonucleotide sequence or well within the interior of the probe. In one example, a probe is synthesized to include an amino ($NH_2$) group on either the 5'- or 3'-end to allow covalent attachment of the probe to a carboxylated solid support. The terminally aminated probes are incubated with the carboxylated particles with the appropriate reagents in order to achieve coupling. The derivatized particles are then collected by either centrifugation or filtration. Other methods of derivatizing the probes and attaching them to a solid support may also be employed. If biotin/streptavidin conjugation is used, the hybridization reaction is conducted prior to conjugation, since the biotin/streptavidin bond is not stable at temperatures greater than 90° C. Alternatively, the target gene may be immobilized on the solid support.

If the area intended for screening is large or the locus is highly polymorphic (mutations may occur anywhere), then the probes will consist of much longer single-stranded DNA fragments which are designed to be complementary to melting temperature domains within the gene or locus being screened. The length and composition of these domain-length probes are determined by thermodynamically modeling the sample wild type gene or locus using a program such as MELT. Next, a wild type sequence is selected for use as a PCR template. In one example, the PCR primer that is incorporated into the sense strand contains a 5'-amino group. Following amplification, the sense strand is covalently attached to a solid support and the antisense strand is removed by denaturation and washing. PCR (or plasmid cloning) is used to amplify both allelic forms of the locus intended for screening. The amplification process can be either linear (single primer) or exponential (two primers), depending upon individual requirements. In the event that fluorescence-based detection is required, the PCR primers are designed such that the primer that will be incorporated into the sense strand of the target will contain a fluor on its 5'-end. Alternatively, other types of labeling, such as radiolabeling or chemiluminescent labeling may also be employed. The presence of a fluor or other label will enhance the sensitivity of detection. Fluors can be excited with ultraviolet illumination, high wattage xenon or krypton lamps or lasers. Alternatively, the target may be visualized by staining the gel with agents such as ethidium bromide, SYBR Green or silver staining. In HPLC, a sufficient mass amount of target will allow detection via absorption. Capillary electrophoresis relies upon a fluorescently labeled target and excitation with a laser.

Capillary electrophoresis (CE) Format

This format is intended to employ either single or multiple capillary instruments, including capillary based automated sequencers. In the simplest scenario, a target fragment is amplified via PCR and a primer with a 5'-fluor is incorporated into the sense strand. If the locus is heterozygous due to mutation, both wild type and mutant allelic target fragments will be synthesized. The labeled target(s) may be washed to remove unincorporated PCR primer and transferred to a tube/microwell containing one or more complementary probes immobilized on a solid support. The sample is thermally cycled to induce hybridization between the labeled target(s) and the immobilized probe(s). Mutant allelic target strands will form heteroduplexes with the probe(s), while wild type allelic target fragments will form homoduplexes. If necessary, free (unannealed) target fragments may be removed by centrifugation, ultrafiltration or other methods prior to analysis. Alternatively, the capillary may simply be prerun and unincorporated target removed electrophoretically prior to the actual analysis. Immediately before analysis, the sample tube/microwell is placed within an appropriate heating device and the sample pre-equilibrated to room or other appropriate temperature (Ti). As analysis begins, a linear temporal temperature gradient is initiated around the tube, gradually raising the temperature of the contents while the flow of current is initiated through the capillary. Along this linear temporal temperature gradient, the Tm of the heteroduplex will be reached first, resulting in deannealing and electrophoretic mobilization of the labeled mutant target strand into the capillary. The temperature is increased linearly over an appropriate period of time until a point (T2) approximately 5–10° C. above the calculated Tm of the homoduplex. Once the Tm of the homoduplex is reached, the wild type target strand deanneals and is mobilized into the capillary. Due to the different times of mobilization, the mutant and wild type target strands are now spatially separated within the capillary and can be distinguished as two independent signals. The fluorescent tags on the target strands are excited and a signal emitted. UV absorption may also be used for detection. The presence of a single signal or peak may indicate a homozygous or wild type sample (i.e. no mutation), while two (or more) signals or peaks per sample indicates the presence of a mutation. A single peak may also be indicative of a mutation if both alleles are mutant. The mutant will however elute at a different time when compared to a reference homozygous wild type control.

In a high-throughput CE format, the PCR-amplified target samples are transferred to a 96- or 384-well (or greater) PCR, ELISA or microwell plate in which the walls and/or well bottom have been modified with bound probe. Alternatively, each well may contain immobilized probe bound to a particulate or other substrate. The plate is placed into a heating device (e.g., thermal cycler) which will allow a linear temporal temperature gradient to be uniformly applied to each well. Because of the ability to use more than one fluor simultaneously, the opportunity to employ multiple fluorescent tags and hence carry out multiplex mutation screening is possible with this method. In this multiplex scenario, each well of the plate may contain more than one species of bound probe, corresponding to either more than one area of one particular gene or to defined areas of several genes. For example, if the polymorphic region of a single gene is 80 base pairs in length, it may be subdivided into four oligonucleotide probes, each 20 nucleotides in length. If necessary, the Tms of the different oligonucleotides used in the multiplex format can be manipulated by changing the lengths to prevent comigration of different labeled fragments. Four sets of PCRs are carried out, each of which will incorporate a different fluorescent tag onto the 5'-end of a sense target strand. In this manner, each fluor represents a different 20-base pair region of the polymorphic area. The presence of single or double signal peaks for each fluor indicates the presence (double peak) or absence (single peak) of a mutation within the respective 20-base pair area.

Alternatively, regions from several different genes (loci) may be screened simultaneously by using multiple fluors. For example, sites of likely mutation from four different genes could be screened by carrying out a separate PCR for each of the four different loci, with each reaction incorporating a different fluor onto the 5'-end of the sense target strand. The respective well of the plate contains four different wild type species of probe, each complementary to one labeled complementary target strand. As the linear temporal temperature gradient is imposed, the heteroduplexes will dissociate first, followed by the homoduplex counterpart. In this manner, each fluor will generate either a single peak if both allelic forms of the locus are wild type or two peaks, if one member of the allelic pair is mutated. Since, in this scenario, several different fragment species are being analyzed, T1 must be lower than the lowest heteroduplex Tm present and T2 must be several degrees higher than the highest homoduplex Tm present. T1=ambient can routinely be used for these analyses. Prior to analysis, the Tms of all homoduplexes intended for simultaneous analyses are calculated in order to determine the appropriate linear temporal temperature range to be applied. If necessary, loading buffers containing denaturants such as urea and/or formamide may be employed to lower the temperatures required for analysis.

Polyacrylamide gel (PAGE) Format

An aliquot of the amplified fragment(s) is (are) combined with an aliquot of the wild type probe-derivatized particles/substrate in an appropriate aqueous buffer and first heated, then cooled in order to achieve hybridization between the labeled sense strand of the PCR product(s) and the complementary immobilized probe. Target PCR strands of wild type sequence will form homoduplexes with the probes, while mutant target strands will form heteroduplexes. The annealed target/probe duplex is then diluted into an appropriate loading buffer and loaded into a well of the gel. Once again, the loading buffer can be supplemented with urea, formamide or other denaturant to lower the temperatures required for analysis.

PAGE analyses are carried out in an acrylamide gel placed within a vertical (or horizontal) electrophoresis apparatus which has been modified to include an element or module programmed to introduce a linear temporal temperature gradient to either the upper area of the gel (wells) in which the samples have been loaded or evenly across the entire area of the gel. In the scenario where only the well area of the gel is subjected to the temporal temperature gradient, a heating module is attached to the front of the gel/plate assembly. This particular apparatus is included in this embodiment of the invention. At T1, even if an electrical field is applied to the gel, the hydrogen-bonded PCR fragments will not exhibit any mobility because they are firmly immobilized onto the particles which are too large to migrate into the polyacrylamide gel matrix. Current is applied to the gel simultaneously with the initiation of the temporal temperature gradient which has been calibrated to increase the temperature of the upper portion of the gel from T1 to T2. Along this linear temperature gradient, the heteroduplex Tms will be reached first, facilitating deannealing and detachment from the solid support and electrophoretic mobilization of the mutant target PCR fragment into the polyacrylamide gel matrix. At some later time/temperature the Tms of the counterpart homoduplexes will be reached, facilitating detachment of the wild type target PCR fragments and their electrophoretic mobilization. Electrophoresis is continued for an appropriate length of time after mobilization of the wild type target PCR fragments to achieve resolution between the mutant and wild type target DNA fragments. The presence of a single signal or peak may indicate a homozygous or wild type sample (i.e. no mutation), while two (or more) signals or peaks per sample indicates the presence of a mutation. A single peak may also be indicative of a mutation if both alleles are mutant. The mutant will however elute at a different time when compared to a reference homozygous wild type control.

Following electrophoresis, the acrylamide gel is illuminated with the appropriate lamp and the number of DNA fragments per lane determined. Where mass amounts permit, the gel may be stained with either ethidium bromide, SYBR Green or other appropriate stain (e.g., silver) and the DNA fragments visualized by illumination with ultraviolet light. Temperature stable agarose formulations and agarose/acrylamide mixtures may also be used.

Electrophoretic analysis may also be carried out using an automated DNA sequencer (e.g., ABI 377) which has been fitted with a module to introduce a linear temporal temperature gradient to the well area of the gel and/or to the entire gel. In this scenario, the target fragments are labeled with an appropriate fluor and data acquisition occurs in real-time, obviating the requirement for gel staining and scanning. This format also allows the use of several different fluors per lane, providing an opportunity for multiplex analysis and increased throughput.

High Performance Liquid Chromatography (HPLC) Format

HPLC analyses employ an HPLC column or reaction cartridge packed with particles or other substrates to which wild type gene-specific probes have been covalently attached. HPLC analysis may be carried out using either a linear temporal temperature gradient or a linear temporal chemical denaturant gradient. When using a linear temporal temperature gradient, the column is housed in an oven or encased in a heating/cooling device (e.g., Peltier) which is in-line with the HPLC instrument and allows the temperature of the column to be controlled. Following PCR amplification, the sample containing target DNA is heated for an appropriate time to facilitate deannealing of the complementary target strands. The denatured sample (target) is then injected into the instrument port and annealed to the immobilized probes at an appropriate temperature. Alternatively, hybridization of the target to the probe may occur in a column/reaction cartridge that is placed into an appropriate heating/cooling device external to the HPLC instrument and the column fitted into the HPLC instrument after hybridization. The flow of solvent through the column is then initiated as the column temperature is simultaneously increased along a linear temporal temperature gradient from T1 to T2. Alternatively, the column may be maintained at a constant temperature and a linear gradient of chemical denaturant(s) introduced over an appropriate period of time. Under a constant flow of solution in the presence of either a linear temperature gradient or a linear chemical denaturant gradient, the heteroduplex will be the first to deanneal and the mutant DNA target fragment mobilized. At a somewhat higher temperature or higher denaturant concentration, the homoduplex will deanneal, resulting in mobilization of the wild type DNA target fragment. The mobilized fragment(s) can be detected by a variety of methods. The presence of a single signal or peak may indicate a homozygous or wild type sample (i.e. no mutation), while two (or more) signals or peaks per sample indicates the presence of a mutation. A single peak may also be indicative of a mutation if both alleles are mutant. The mutant will however elute at a different time when compared to a reference homozygous wild type control.

In order to achieve automation of mutation screening, an upstream combination thermal cycler/autosampler may be used. PCR amplification and sample denaturation occur within this module, allowing multiple subject samples to be amplified and screened unattended.

Microfluidics Format

In another embodiment, the probe or target is be localized within a region of a microfluidic device, incorporating single or mutiple channels on a solid substrate. Such devices are disclosed, for example, in U.S. Pat. Nos. 6,153,013; 6,180,536; and 6,186,660. Complementary probe or target is introduced and hybridization induced. Alternatively, hybridization may be carried out at a separate work station, independent of the microfluidic device. Either a chemical or thermal gradient is imposed and the separated deannealed products are detected. This format is conducive to rapid, high throughput analyses.

Although the foregoing invention has been described in some detail by way of illustration for purposes of clarity and understanding, it will be obvious that certain changes and modifications may be practiced within the scope of the appended claims.

What is claimed is:

1. A method of detecting single nucleotide polymorphisms, said method comprising:
    a) admixing a nucleotide probe with a sample containing target wild type polynucleotide(s) and target mutant polynucleotide(s), said probe having a nucleotide sequence complementary to at least a portion of one strand of the mutant or wild type polynucleotide(s);
    b) inducing hybridization between the probe and the target wild type polynucleotide(s) and between the probe and target mutant polynucleotide(s), thereby forming a first duplex between the probe and the target wild type polynucleotide(s) and forming a second duplex between the probe and the target mutant polynucleotide(s), wherein target wild type polynucleotide(s) form homoduplexes with said probe having a nucleotide sequence complementary to the wild type polynucleotide(s) and target mutant polynucleotide(s) form heteroduplexes with said probe having a nucleotide sequence complementary to the wild type polynucleotide(s), while target mutant polynucleotide(s) form homoduplexes with said probe having a nucleotide sequence complementary to the mutant polynucleotide(s) and target wild type polynucleotide(s) form heteroduplexes with said probe having a nucleotide sequence complementary to the mutant polynucleotide(s);

c) applying a linear temporal temperature gradient to the sample to induce selective denaturation of the first and second duplex, wherein said heteroduplexes and said homoduplexes are subjected to one of an electrical field and a flow of solvent: and d) comparing the sample to a reference polynucleotide(s) in order to detect the presence of the wild type and mutant polynucleotide(s).

2. The method of claim 1 in which the gradient is a thermal gradient.

3. The method of claim 1 in which the probe is attached to a solid support.

4. The method of claim 1 in which the target polynucleotide(s) are immobilized to a solid support.

5. The method of claim 1 employing capillary electropheresis, gel electropheresis, chromatography, or microfluidics for identification of separated strands of polynucleotide(s).

6. A method of detecting single nucleotide polymorphisms, said method comprising:

a) admixing a nucleotide probe with a sample containing target wild type polynucleotide(s) and target mutant polynucleotide(s), said probe having a nucleotide sequence complementary to at least a portion of one strand of one of the mutant or wild type polynucleotide(s);

b) inducing hybridization between the probe and the target wild type polynucleotide(s) and between the probe and target mutant polynucleotide(s), thereby forming a first duplex between the probe and the target wild type polynucleotide(s) and forming a second duplex between the probe and the target mutant polynucleotide(s), wherein target wild type polynucleotide(s) form homoduplexes with said probe having a nucleotide sequence complementary to the wild type polynucleotide(s) and target mutant polynucleotide(s) form heteroduplexes with said probe having a nucleotide sequence complementary to the wild type polynucleotide(s), while target mutant polynucleotide(s) form homoduplexes with said probe having a nucleotide sequence complementary to the mutant polynucleotide(s) and target wild type polynucleotide(s) form heteroduplexes with said probe having a nucleotide sequence complementary to the mutant polynucleotide(s);

c) applying a linear thermal gradient to the sample to induce selective denaturation of the first and second duplex, wherein said heteroduplexes and said homoduplexes are subjected to one of an electrical field and a flow of solvent; and d) comparing the sample to a reference polynucleotide(s) in order to detect the presence of the wild type and mutant polynucleotide(s).

7. The method of clam 6 in which the probe is attached to a solid support.

8. The method of claim 6 in which the target polynucleotide(s) are immobilized to a solid support.

9. The method of claim 6 employing capillary electropheresis, gel electropheresis, chromatography, or microfluidics for identification of separated strands of polynucleotide(s).

10. A method of detecting single nucleotide polymorphisms, said method comprising:

a) admixing a nucleotide probe with a sample containing target wild type polynucleotide(s) and target mutant polynucleotide(s), said probe having a nucleotide sequence complementary to at least a portion of one strand of the wild type polynucleotide(s);

b) inducing hybridization between the probe and the target wild type polynucleotide(s) and between the probe and target mutant polynucleotide(s), thereby forming a first duplex between the probe and the target wild type polynucleotide(s) and forming a second duplex between the probe and the target mutant polynucleotide(s), wherein target wild type polynucleotide(s) form homoduplexes with said probe having a nucleotide sequence complementary to the wild type polynucleotide(s) and target mutant polynucleotide(s) form heteroduplexes with said probe having a nucleotide sequence complementary to the wild type polynucleotide(s);

c) applying a linear thermal gradient to the sample to induce selective denaturation of the duplexes, wherein said heteroduplexes and said homoduplexes are subjected to one of an electrical field and a flow of solvent; and d) comparing the sample to a reference polynucleotide(s) in order to detect the presence of the wild type and mutant polynucleotide(s).

11. The method of claim 10 in which the target polynucleotide(s) are immobilized to a solid support.

12. A method of detecting single nucleotide polymorphisms, said method comprising:

a) admixing a nucleotide probe with a sample containing target wild type polynucleotide(s) and target mutant polynucleotide(s), said probe having a nucleotide sequence complementary to at least a portion of one strand of the mutant polynucleotide(s);

b) inducing hybridization between the probe and the target wild type polynucleotide(s) and between the probe and target mutant polynucleotide(s) thereby forming a first duplex between the probe and the target wild type polynucleotide(s) and forming a second duplex between the probe and the target mutant polynucleotide(s), wherein target mutant polynucleotide(s) form homoduplexes with the said probe having a nucleotide sequence complementary to the mutant polynucleotide(s) and target wild type polynucleotide(s) form heteroduplexes with said probe having a nucleotide sequence complementary to the mutant polynucleotide(s);

c) applying a linear thermal gradient to the sample to induce selective denaturation of the duplexes, wherein said heteroduplexes and said homoduplexes are subjected to one of an electrical field and a flow of solvent; and d) comparing the sample to a reference polynucleotide(s) in order to detect the presence of the wild type and mutant polynucleotide(s).

13. The method of claim 12 which the target polynucleotide(s) are immobilized to a solid support.

14. A method of detecting single nucleotide polymorphisms, said method comprising:
   a) admixing a nucleotide probe with a sample containing target wild type polynucleotide(s) and target mutant polynucleotide(s), said probe having a nucleotide sequence complementary to at least a portion of one strand of one of the mutant or wild type polynucleotide(s), wherein said target polynucleotide(s) are attached to a solid support;
   b) inducing hybridization between the probe and the target wild type polynucleotide(s) and between the probe and target mutant polynucleotide(s), thereby forming a first duplex between the probe and the target wild type polynucleotide(s) and forming a second duplex between the probe and the target mutant polynucleotide(s), wherein target wild type polynucleotide(s) form homoduplexes with said probe having a nucleotide sequence complementary to the wild type polynucleotide(s) and target mutant polynucleotide(s) form heteroduplexes with said probe having a nucleotide sequence complementary to the wild type polynucleotide(s) while target mutant polynucleotide(s) form homoduplexes with said probe having a nucleotide sequence complementary to the mutant polynucleotide(s) and target wild type polynucleotide(s) form heteroduplexes with said probe having a nucleotide sequence complementary to the mutant polynucleotide(s);
   c) applying a linear thermal gradient to the sample to induce selective denaturation of the duplexes, wherein said heteroduplexes and said homoduplexes are subjected to one of an electrical field and a flow of solvent;
   d) eluting said single stranded polynucleotide(s) from said solid support;
   e) comparing the elution time of said single stranded polynucleotide(s) to polynucleotide(s) in order to detect the presence of the wild type and mutant polynucleotide(s).

15. The method of claim 14 in which the target polynucleotide(s) are immobilized to a solid support.

* * * * *

UNITED STATES PATENT AND TRADEMARK OFFICE
CERTIFICATE OF CORRECTION

PATENT NO.      : 6,596,487 B2
DATED           : July 22, 2003
INVENTOR(S)     : Saeedullah Mohammad Raees and Brian Alfred Perry It is certified that error appears in the above-identified patent and that said Letters Patent is hereby corrected as shown below:

<u>Title page,</u>
Item [74], *Attorney, Agent, or Firm*, "McGinn & Gibb, PLLC; Mohammed S. Rahman, Esq." should read -- McGinn & Gibb, PLLC; Mohammad S. Rahman, Esq. --

<u>Column 13,</u>
Line 1, the word -- in -- should be inserted before the word "which".

<u>Column 14,</u>
Line 16, step (e), the phrase -- that of a reference -- should be inserted after the phrase "comparing the elution time of said single stranded polynucleotide(s) to"

Signed and Sealed this

Fourth Day of November, 2003

JAMES E. ROGAN
*Director of the United States Patent and Trademark Office*